United States Patent
Distler et al.

(10) Patent No.: US 7,200,204 B2
(45) Date of Patent: Apr. 3, 2007

(54) DIAPHRAGM FASTENING DEVICE AND COMPUTED TOMOGRAPHY APPARATUS EMBODYING SAME

(75) Inventors: Friedrich Distler, Fürth (DE); Ulrich Kühn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/140,834

(22) Filed: May 31, 2005

(65) Prior Publication Data
US 2006/0104421 A1    May 18, 2006

(30) Foreign Application Priority Data
Nov. 15, 2004   (DE)   ....................... 10 2004 055 022

(51) Int. Cl.
*G21K 7/00* (2006.01)
(52) U.S. Cl. ....................................... 378/156; 378/119
(58) Field of Classification Search ................ 378/4, 378/147–153, 82–90, 119, 156
See application file for complete search history.

(56) References Cited
U.S. PATENT DOCUMENTS 4,532,645 A * 7/1985 Morris ..................... 378/147
6,061,419 A * 5/2000 Hsieh et al. ................... 378/4
6,257,762 B1 * 7/2001 Guzik ......................... 378/203
6,396,902 B2 * 5/2002 Tybinkowski et al. ...... 378/150

FOREIGN PATENT DOCUMENTS

| DE | G 83 10 177 U1 | 10/1983 |
| DE | 295 08 129 U1 | 10/1995 |
| DE | OS 102 42 920 | 3/2004 |
| DE | OS 102 44 898 | 4/2004 |

* cited by examiner

*Primary Examiner*—Edward J. Glick
*Assistant Examiner*—Hoon Song
(74) *Attorney, Agent, or Firm*—Schiff Hardin LLP

(57) ABSTRACT

A fastening device for a diaphragm for x-ray radiation has a base plate provided with an opening for the passage of x-ray radiation, the base plate being able to accommodate load forces, and at least one covering device which can be arranged for enclosure of a space on the base plate. A diaphragm can be housed in the space. A computer tomography apparatus embodies such a fastening device for a diaphragm.

18 Claims, 4 Drawing Sheets

DIAPHRAGM FASTENING DEVICE AND COMPUTED TOMOGRAPHY APPARATUS EMBODYING SAME

BACKGROUND OF THE INVENTION

1. Field of the Invention

The present invention concerns a fastening device for a diaphragm for x-ray radiation as well as a computed tomography apparatus having a radiation source with a diaphragm for x-ray radiation mounted on such a fastening device.

2. Description of the Prior Art

X-ray computed tomography apparatuses known from German OS 102 42 920 and German OS 102 44 898 have comprise a rotatable frame on which an x-ray source and an x-ray detector are disposed opposite one another. A patient bed on which the patient is positioned is moved through a patient opening of the rotary frame to acquire, for example, diagnostic x-ray images of a patient, with a number of x-ray projections of a body region of the patient being acquired from different projection directions. Slice images of the body region of the patient or volume representations can be reconstructed from the acquired x-ray projections of the body region.

In a diagnostic examination with an x-ray computed tomography apparatus, the patient is located on a patient bed in the patient opening of the rotary frame, or move through the patient opening. In order to alleviate feelings of spatial confinement as well as to enable more space for the medical personnel in the region of the patient opening for medical measures, as well as also to make it easier to examine particularly corpulent persons by means of x-ray computed tomography, there is a desire to enlarge the patient opening. The outer diameter of the rotating rotary frame, however, should not be enlarged. At the same time, the rotation speed of the rotary frame should be increased in order to develop new application fields for computed tomography, for example in cardiology. Both the enlargement of the patient opening and the increase of the rotation speed of the rotary frame require design changes to presently-used x-ray computed tomography apparatuses.

A known radiator diaphragm 1 associated with an x-ray source arranged on a rotary frame is shown in FIG. 1. Conventionally it is arranged with a filter unit 2 (separated by a non-load bearing intermediate plate 3) in a housing 4 requiring a relatively large space. The housing 4 is conventionally fashioned from a several millimeter thick steel plate and, apart from openings for the passage of x-ray radiation, is provided with an x-ray-shielding material. The non-load bearing intermediate plate 3 that separates the filter unit 2 from the radiator diaphragm 1 is fastened in the supporting and scatter-radiation-sealed housing 4 with angle supports 5, as can be seen in the section view of FIG. 2. The massive housing 4 has not only a high space requirement on the rotary frame, which is disadvantageous with regard to the size of the patient opening, but also has a mass of several kilograms, which is also disadvantageous with regard to angular momentum on the rotary frame. High centrifugal forces must be accommodated by the fastening means with which the housing is fastened on the rotary frame.

SUMMARY OF THE INVENTION

An object of the present invention is to provide a fastening device for a diaphragm for x-ray radiation, preferably for a computed tomography apparatus, which has an optimally low space requirement with an optimally low dead weight.

This object is achieved in accordance with the invention by a fastening device for a diaphragm for x-ray radiation, having a base plate with an opening for the passage of x-ray radiation that can accommodate load forces, and at least one covering device disposed to enclose a space at the base plate, whereby a diaphragm can be contained in the space. According to the invention the conventional massive housing for the diaphragm for x-ray radiation is thus foregone, and instead a base plate that can be attached to the rotary frame is used the diaphragm for x-ray radiation being arranged at the base plate. The base plate is designed, with regard to the material used and the material strength, such that it can accommodate the load forces necessary for retention of the diaphragm. A covering device that is arranged on the base plate is provided for incorporation of the diaphragm. Since the inventive fastening device essentially has only a base plate and a covering device, it can be constructed more easily than the known diaphragm housings and moreover requires a smaller space, such that the aforementioned requirements are met, both to enlarge the patient opening of the computed tomography apparatus and (as a consequence of the reduced mass) to achieve an increase of the rotation speed of the rotary frame of the computed tomography apparatus.

According to a preferred embodiment of the invention, at least one side wall is present on at least one side of the base plate, and the covering device is attached to the base plate and/or to the side wall to enclose the space.

In an embodiment of the invention at least one side wall is present on each side of the base plate and the fastening device has a second covering device so that spaces for accommodation of components are present on both sides of the base plate in order to achieve a shaping of the x-ray beam as well as to be able to influence the intensity and the spectrum of the x-ray radiation. The inventive fastening device thereby allows the components to be arranged relatively close to the x-ray source.

In a preferred embodiment of the invention two side walls are on each side of the base plate on both sides of the opening, providing a U-shaped profile on both sides of the base plate. The U-shaped profiles can be sealed with the covering device. The U-shaped profile is particularly inflexible with regard to deformation. The side walls on both sides of the base plate preferably are arranged such that a double-U-shaped profile results. The description of the side walls as being present on both sides of the opening encompasses the side walls being attached at the edges of the opening, thus in the opening.

In an embodiment of the invention, the covering devices for sealing of the U-shaped profiles of the base plate are likewise fashioned U-shaped.

As a consequence of the provision of two spaces in the fastening device, in a variant of the invention the diaphragm for x-ray radiation can be arranged in a space that can be sealed with a covering device and a beam filter for x-ray radiation can be arranged in the other space that can be sealed with a covering device.

In one embodiment of the invention, the covering devices each have an opening for the passage of x-ray radiation therethrough. Moreover, the covering devices are thin-walled to save weight such that, although they are dimensionally stable and suitable for sealing a space, they can themselves accommodate no load forces for retention of components such as diaphragms or filter devices.

In another embodiment of the invention, the covering devices are fashioned of a self-supporting material that is permeable to x-ray radiation, and this material is provided with a layer of an x-ray-shielding material (preferably lead). A weight saving is achieved in this manner, as is a scatter-radiation-sealed closure of the spaces.

Likewise for weight-saving, the base plate and/or the side walls can be composed of aluminum. The base plate and the side walls can form one unit, for example in the form of a cast part. The side walls alternatively can be attached to the base plate by known fastening means, for example with screws. For scatter-radiation the side walls can have a layer of an x-ray-radiation-shielding material (preferably lead).

The above object also is achieved by a computed tomography apparatus having a rotary frame on which an x-ray source and an x-ray detector are mounted opposite one another, and a diaphragm which is arranged on a fastening device, associated with the x-ray source of the type described above.

DESCRIPTION OF THE PREFERRED EMBODIMENTS

Figure 1:
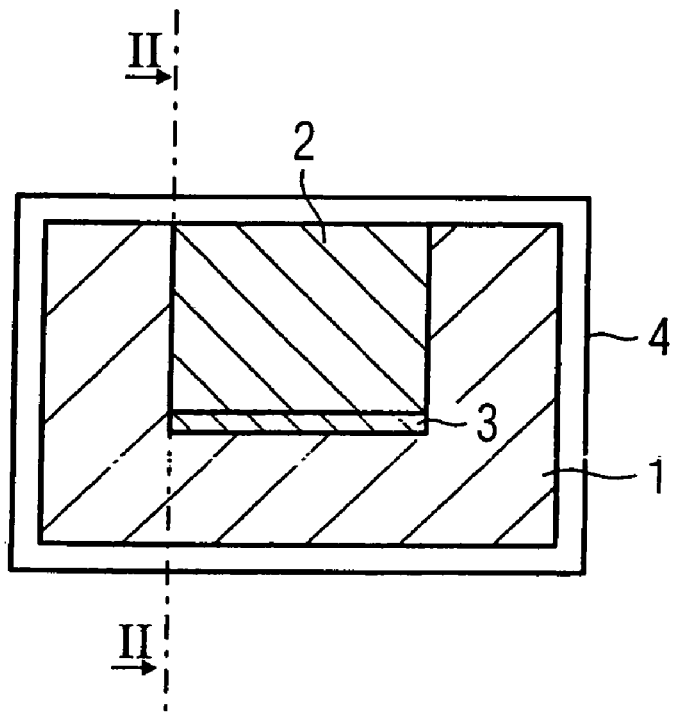
FIG. 1 is a partially sectional representation of a diaphragm device according to the prior art.
Figure 2:
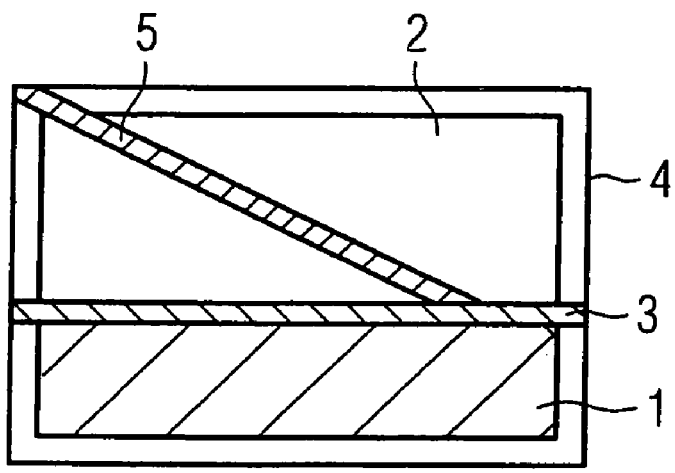
FIG. 2 is a sectional view along line II—II of FIG. 1 of the diaphragm device of FIG. 1.

The x-ray computed tomography apparatus shown in FIG. 3 has an acquisition unit with an x-ray source 11 from the focus F of which x-ray radiation originates that is shaped into a fan-shaped x-ray beam 12 with a fan angle α by a diaphragm explained below and not explicitly shown in FIG. 3. Moreover, the acquisition unit has an x-ray detector 13 that, in a known manner, has a number of rows of detector elements successively arranged in the direction of the system axis Z of the computed tomography apparatus. The x-ray source 11 and the x-ray detector 13 are disposed opposite one another on a rotary frame 18, which is the rotatable part of the gantry of the computed tomography apparatus. In the exemplary embodiment, a patient P is shown on a patient bed 16 of the computed tomography apparatus. The patient bed 16 can be displaced in the direction of the system axis Z of the computer tomography apparatus, whereby this patient bed 16 moves through a patient opening 17 of the rotary frame 18 of the computed tomography apparatus. The rotary frame 18 is mounted such that it can rotate around the system axis Z of the computed tomography apparatus and is rotated around the system axis Z in the (φ-direction to scan the patient P with x-ray radiation. X-ray projections of a body region of the patient P are acquired from different projection directions. The x-ray beam 12 irradiates an imaging field 10 of a circular cross section. The data of the x-ray projections acquired with the x-ray detector 13 are supplied to a computer 14 with which slice images or volume representations of acquired body regions of the patient P can be reconstructed in a known manner from the measurement data and displayed on a display device 19. The rotary frame 18 is driven by a motor 15 in a manner schematically shown in FIG. 3

Figure 3:
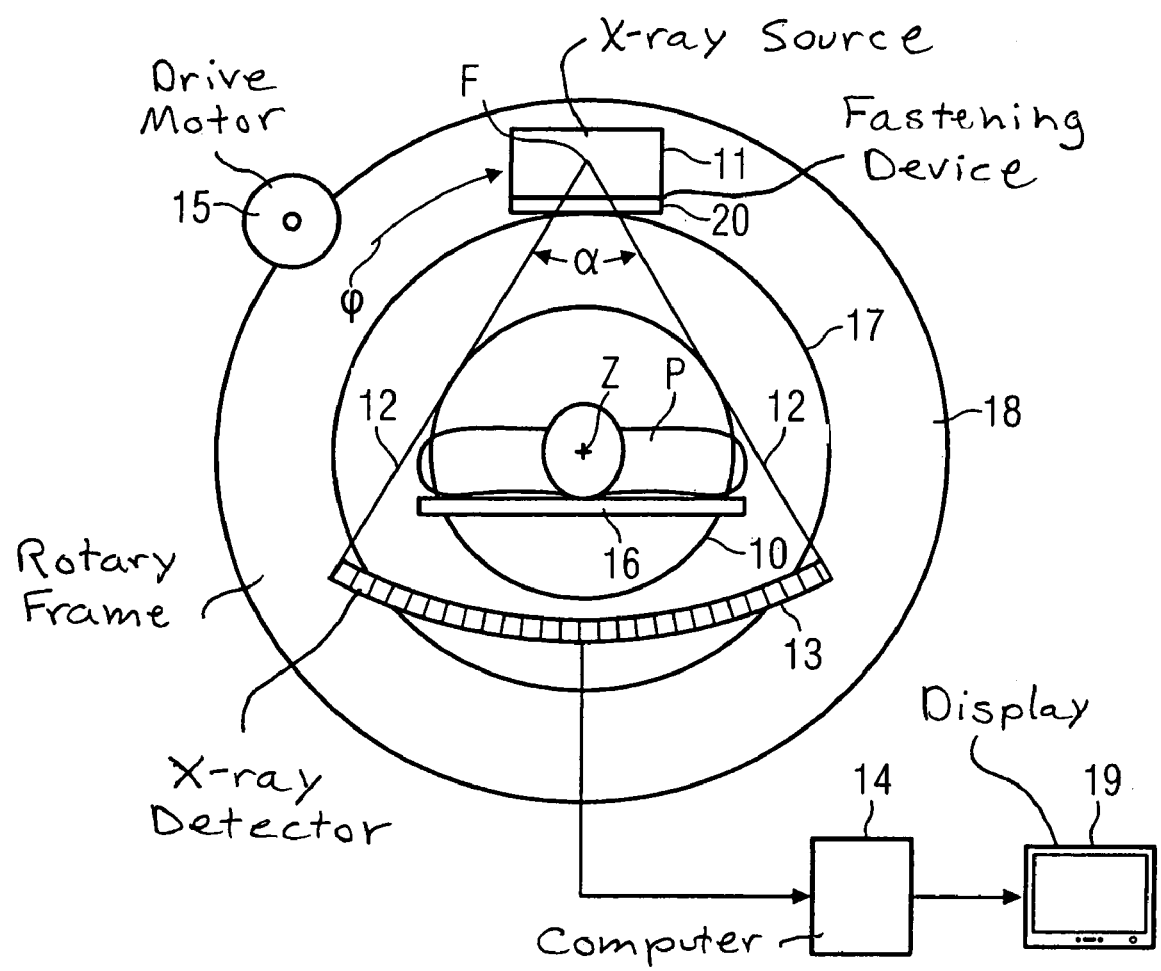
FIG. 3 is a schematic illustration of an inventive computer tomography apparatus.

As can be seen from FIG. 3, an inventive fastening device for the mentioned diaphragm (which is shown only schematically in FIG. 3) is associated with the x-ray source 11 on the rotary frame 18.

Figure 4:
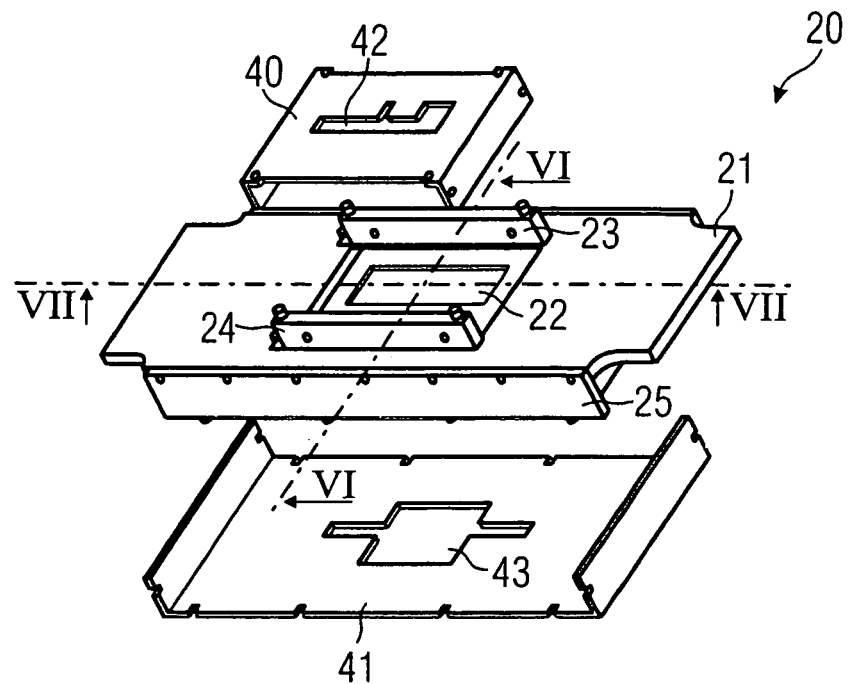
FIG. 4 is a view from above of an inventive fastening device.
Figure 5:
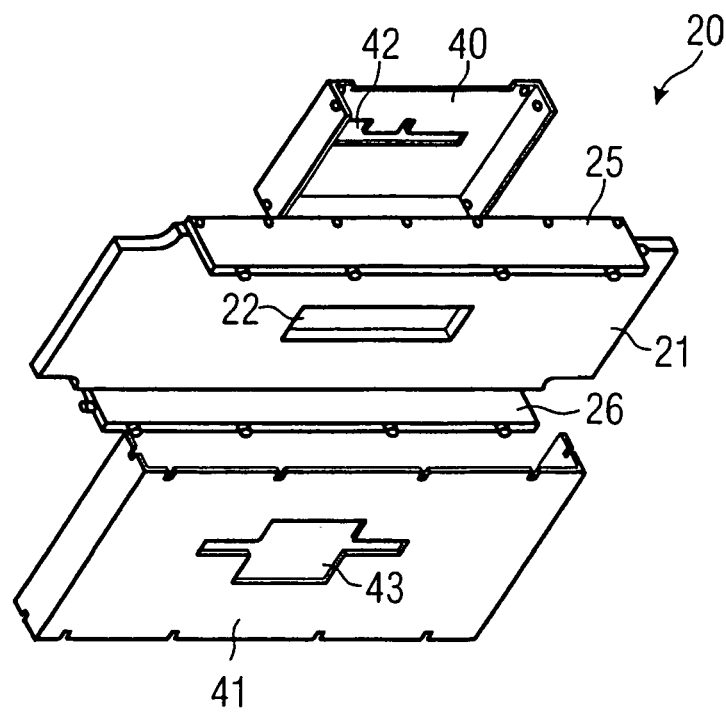
FIG. 5 is a view from below of an inventive fastening device.

As can be seen from FIGS. 4 and 5, the fastening device 20 has a base plate 21 with an opening 22. According to the exemplary embodiment shown in FIGS. 4 and 5, two side walls are respectively provided on each side of the base plate 21, thus on the upper side and the lower side, and in fact both sides of the opening 22, such that (as can be seen from FIG. 6) a double-U profile of the fastening device results. In the exemplary embodiment, the side walls 23 through 26 are respectively attached to the base plate 21 with screws (not shown in detail). The side walls 23 and 24 are arranged in a slot in the base plate 21 that is preferably produced via milling. The unit composed of the base plate 21 and the side walls 23 through 26 also can be manufactured as one piece, for example as a cast unit. Given a separate execution of the side walls 23 through 26 from the base plate 21, the side walls 23 through 26 can be connected to the base plate 21 with other fastening means or connection methods, for example by welding. The base plate 21 as well as the side walls 23 through 26 are formed of solid aluminum in the case of the present exemplary embodiment. The base plate 21 as well as the side walls 23 through 26 preferably exhibit a thickness of 5 to 10 mm. Fashioning the base plate 21 and of the side walls 23 through 26 from aluminum has the advantage that aluminum is a material that can be easily processed and exhibits a relatively low dead weight. The execution of the fastening device with a double-U profile has the advantage that it is very rigid with regard to deformation.

Figure 6:
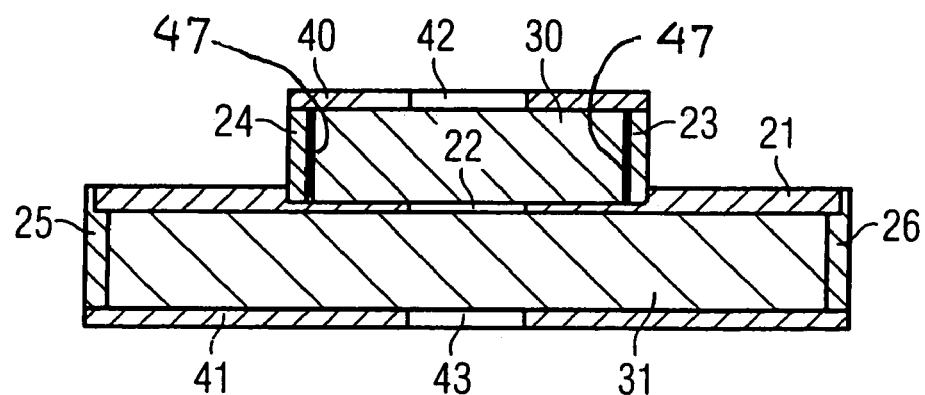
FIGS. 6 and 7 are sectional views along lines VI—VI and VII—VII, respectively of FIG. 4, of the inventive fastening device in an assembled state containing components.
Figure 7:
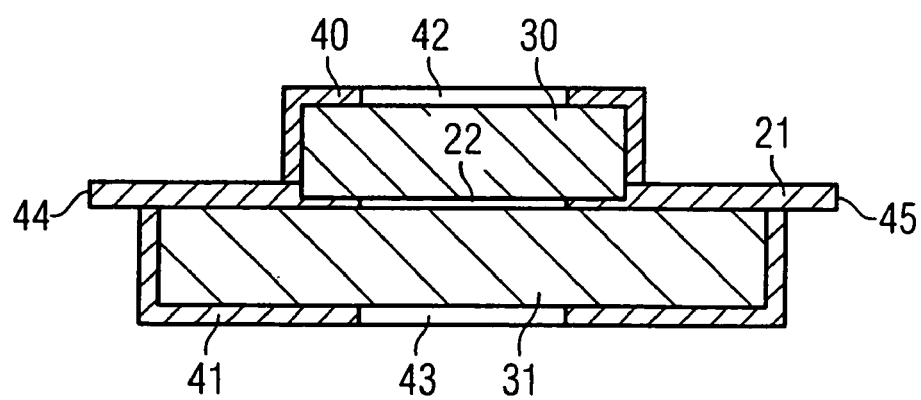

For protection from scatter radiation, in the exemplary embodiment both sides of the base plate 21 and the inner side of the side walls 23 through 26 are provided with x-ray-shielding material 47 layer of lead in the present case, as shown in FIG. 6. As can be seen from FIGS. 6 and 7, in the exemplary embodiment a filter 30 for filtering the x-ray radiation is disposed on the upper side of the base plate 21 between the side walls 23 and 24. The filter 13 is a known filter formed, for example, from aluminum, titanium or stainless steel that serves for filter of the x-ray radiation depending on the desired examination type. A diaphragm 31 that has a number of diaphragm plates that can be moved relative to one another to shape the x-ray beam is disposed on the underside of the base plate 21 between the side walls 25 and 26. Diaphragms that can be arranged on the fastening device are known, for example, from German OS 102 44 898 and German OS 102 42 920. The filter 30 and the diaphragm 31 each can be fastened (for example with screws) both to the base plate 21 and to the side walls 23, 24, or 25, 26, for fixing to the fastening device 20.

To enclose the ray filter 30 and the diaphragm 31, covering devices 40 and 41 are provided which are fashioned U-shaped in the exemplary embodiment. The covering devices 40 and 41 respectively have openings 42 and 43 for the unhindered passage of x-ray radiation. The covering devices 40, 41 are thin-walled in the exemplary embodiment such that, although these are dimensionally stable, they can accommodate no load forces with regard to the diaphragm 31 or the filter 30, which is not necessary since the load forces are completely accommodated by the base plate 21 and the side walls 23 through 26. As a result of the thin-walled execution of the covering devices 40, 41, which are preferably fashioned from a metallic material, the weight of the fastening device can be reduced. For protection from scatter radiation, in the exemplary embodiment the covering devices 40 and 41 are provided on their inner sides with an x-ray-shielding material, preferably with a layer of lead, which likewise is no explicitly shown in the figures. If the covering devices 40 and 41 are ultimately connected (for example screwed together) with the side walls 23 and 24 and 25 and 26, a scatter radiation-sealed closure ensues of the spaces in which the filter 30 or the diaphragm 31 are disposed. The fastening device 20 provided with the filter 30 and the diaphragm 31 can ultimately be fastened to suitable mountings (not shown in the figures) of the rotary frame 18 with the base plate 21 in association with the x-ray source 11, as is schematically shown in FIG. 3. The supports 44, 45 of the base plate 21 that can be seen in FIG. 7 that serve for attachment of the base plate 21 and thus the fastening device 20 to the rotary frame 18.

Space is saved and weight is reduced by the inventive fastening device 20 in comparison to a diaphragm box of a conventional computed tomography apparatus, such that the requirements are met to execute the patient opening larger in comparison to the patient opening of conventional computed tomography apparatuses and to reduce the mass on the rotary frame 18, which has an advantageous effect for higher rotation speeds of the rotary frame 18.

As an alternative to the fastening device described in the exemplary embodiment, the side walls of the fastening device on the upper side and lower side can be arranged offset from one another by 90° such that, although a double-U profile does not result, a U-shaped profile results both on the upper side and on the lower side, so a high deformation rigidity still can be attained.

As another alternative, side walls do not necessarily have to be present. Instead, the diaphragm and/or the filter can be fastened only to the base plate and be enclosed with a corresponding hollow cuboid-shaped covering device (preferably open at the top). The covering devices in this case preferably have notches in order to be able to simply attach covering devices to the base plate, for example by means of screws.

In the variants with side walls, the side walls do not have to be arranged on both sides of the base plate. In the event that a filter is not necessary, one or more side walls that serve for attachment of a diaphragm can be arranged, for example, only on one side of the base plate.

Moreover, it can be sufficient for only one side wall to be present on each side, which side wall serves together with the base plate for the arrangement of a filter or a diaphragm.

A number of side walls for attachment of a diaphragm or a ray filter can also be present on each side of the base plate.

The base plate as well as the side walls thereby do not necessarily have to be fashioned from aluminum. Rather, other metals or dimensionally stable materials that can provide the load forces necessary for a diaphragm or a filter are also suitable as materials for the base plate and the side walls.

Furthermore, the coating of the base plate as well as the side walls (insofar as the side wall material is not itself x-ray-shielding) does not necessarily have to ensue with lead. Other x-ray-shielding materials can be used for the coating.

The side walls need exhibit no coating with an x-ray-shielding material if shielding plates made from an x-ray-shielding material are associated with the side walls. The shielding plates are, for example, applied to the side walls or are even part of the covering devices.

The covering devices likewise do not necessarily have to be fashioned U-shaped, but rather, dependent on the number of the side walls, can exhibit a shape that is suitable for closure of the space accommodating the ray filter or the diaphragm. Dependent on the material used for the covering device, the suitable wall thickness is selected that ensures the necessary dimensional stability for the covering devices. The covering devices also do not necessarily have to be coated with lead, but alternatively can be provided (to the extent necessary) with a different x-ray-shielding material.

Although modifications and changes may be suggested by those skilled in the art, it is the intention of the inventors to embody within the patent warranted hereon all changes and modifications as reasonably and properly come within the scope of their contribution to the art.

We claim as our invention:

1. A fastening device for an x-ray radiation diaphragm, comprising:
   a base plate adapted for mounting relative to an x-ray source that emits x-ray radiation, said base plate having an opening therein allowing passage of said x-ray radiation therethrough, said base plate being comprised of load-bearing material;
   a covering device fitted onto said base plate and defining an enclosure, in combination with said base plate, communicating with said opening and adapted to contain an x-ray radiation diaphragm therein;
   said base plate having a base plate surface and a first side wall projecting from a first side of said base plate surface and a second side wall projecting from a second side of said base plate surface;
   said covering device comprising a first cover attached to said first side wall at said first side of said base plate surface, and a second cover attached to said second side wall at said second side of said base plate surface; and
   said enclosure comprising a first enclosure portion defined by said first covering and said base plate, and adapted to contain a radiation filter therein, and a second enclosure portion, defined by said base plate and said second cover, and adapted to contain said radiation diaphragm therein.

2. A fastening device as claimed in claim 1 wherein said base plate has a base plate surface and a side wall projecting from said base plate surface, said covering device being attached to said side wall.

3. A fastening device as claimed in claim 1 wherein said covering device has an opening therein, substantially aligned with said opening in said base plate allowing passage of said x-ray radiation therethrough.

4. A fastening device as claimed in claim 1 wherein said covering device consists of a plurality of dimensionally stable but non-load bearing walls.

5. A fastening device as claimed in claim 4 wherein said covering device is comprised of an x-ray permeable material covered by a coating of an x-ray shielding material.

6. A fastening device as claimed in claim 5 wherein said covering device is covered at least at one side thereof with a layer of lead, forming said x-ray shielding material.

7. A fastening device as claimed in claim 1 wherein said base plate consists of aluminum.

8. A fastening device as claimed in claim 1 wherein said base plate comprises a base plate surface with a side wall projecting therefrom, to which said covering device is attached, said side wall consisting of aluminum.

9. A fastening device as claimed in claim 8 comprising a layer of x-ray shielding material on said side wall.

10. A fastening device as claimed in claim 9 wherein said x-ray shielding material comprises lead.

11. A fastening device for an x-ray radiation diaphragm, comprising:
- a base plate adapted for mounting relative to an x-ray source that emits x-ray radiation, said base plate having an opening therein allowing passage of said x-ray radiation therethrough, said base plate being comprised of load-bearing material;
- a covering device fitted onto said base plate and defining an enclosure, in combination with said base plate, communicating with said opening and adapted to contain an x-ray radiation diaphragm therein: and
- said base plate having a base plate surface and two first side walls projecting from a first side of said base plate surface at opposite sides of said opening, forming a first U-shaped profile at said first side of said base plate, and two second sidewalls projecting from a second side of said base plate at opposite sides of said opening forming a second U-shaped profile at said second side of said base plate, and said covering device comprising a first cover attached to said two first side walls and a second cover attached to said two second side walls.

12. A fastening device as claimed in claim 11 wherein said first cover has a U-shaped cross-section substantially adapted to match said first U-shaped profile, and wherein said second cover has a U-shaped cross-section substantially adapted to match said second U-shaped profile.

13. A fastening device as claimed in claim 11 wherein said covering device has an opening therein, substantially aligned with said opening in said base plate allowing passage of said x-ray radiation therethrough.

14. A fastening device as claimed in claim 11 wherein said covering device consists of a plurality of dimensionally stable but non-load bearing walls.

15. A fastening device as claimed in claim 14 wherein said covering device is comprised of an x-ray permeable material covered by a coating of an x-ray shielding material.

16. A fastening device as claimed in claim 15 wherein said covering device is covered at least at one side thereof with a layer of lead, forming said x-ray shielding material.

17. A fastening device as claimed in claim 11 wherein said base plate consists of aluminum.

18. A computed tomography apparatus comprising: a rotary frame;
- an x-ray source and an x-ray detector mounted on said rotary frame opposite each other, said x-ray source emitting x-ray radiation;
- a radiator filter;
- a diaphragm for gating said x-ray radiation;
- a fastening device for said diaphragm having a base plate mounted relative to said x-ray source, said base plate having an opening therein allowing passage of said x-ray radiation therethrough, said base plate being comprised of load-bearing material, and a covering device attached to said base plate and defining, in combination with said base plate an enclosure in which said diaphragm is contained; and
- said covering device of said fastening device comprising a first cover attached to a first side of said base plate and defining a first portion of said enclosure, in which said radiation filter is contained, and a second cover, attached to a second side of said base plate, opposite said first side, defining a second portion of said enclosure in which said diaphragm is contained.

* * * * *